United States Patent [19]

Morrison

[11] 4,244,357
[45] Jan. 13, 1981

[54] METHOD AND APPARATUS FOR HOMOGENEOUSLY IRRADIATING THE VAGINAL MUCOSA WITH A LINEAR SOURCE UTEROVAGINAL APPLICATOR

[76] Inventor: Richard A. Morrison, 9021 Delmar, Shawnee Mission, Kans. 66207

[21] Appl. No.: 1,160

[22] Filed: Jan. 5, 1979

[51] Int. Cl.³ .............................................. A61N 5/10
[52] U.S. Cl. ..................................................... 128/1.2
[58] Field of Search .................................. 128/1.1, 1.2

[56] References Cited
U.S. PATENT DOCUMENTS

| 2,544,939 | 3/1951 | Ritala | 128/1.2 |
| 3,323,511 | 6/1967 | Holter | 128/1.2 |
| 3,789,829 | 2/1974 | Hasson | 128/1.2 |

FOREIGN PATENT DOCUMENTS 7604831  11/1974  Netherlands .............................. 128/1.1

OTHER PUBLICATIONS

Redpath et al., "British Journal of Radiology" vol. 49, No. 587, Nov. 1976, pp. 963–965.

Primary Examiner—William E. Kamm
Attorney, Agent, or Firm—Schmidt, Johnson, Hovey & Williams

[57] ABSTRACT

Cancer of the uterine cervix is treated with a combination of external beam radiation to the pelvis and a linear source uterovaginal applicator which utilizes the maximum distance available between the source and vaginal mucosa, thus achieving an improved percentage depth dose as well as dose homogeneity around the entire circumference of the vaginal vault.

14 Claims, 4 Drawing Figures

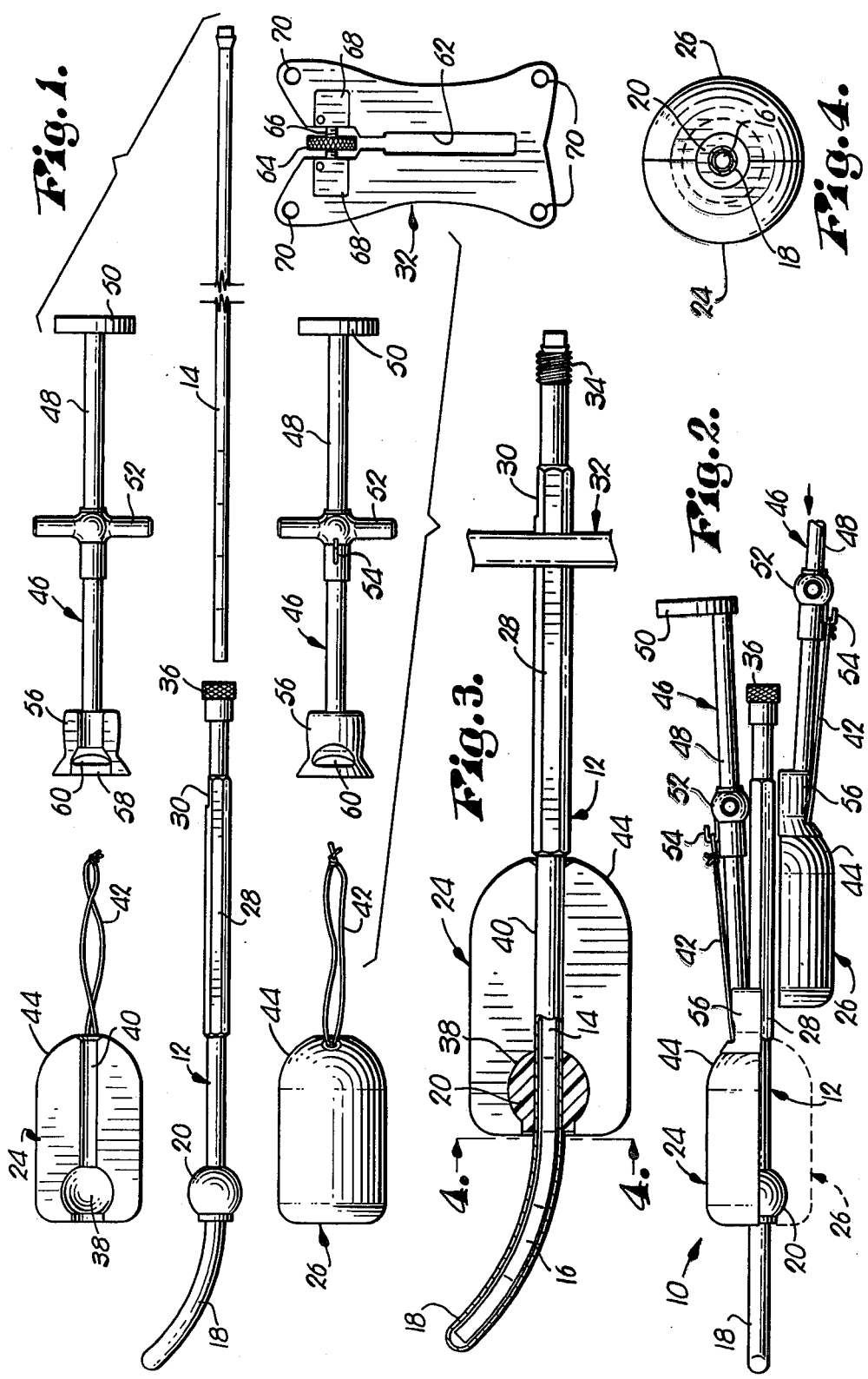

METHOD AND APPARATUS FOR HOMOGENEOUSLY IRRADIATING THE VAGINAL MUCOSA WITH A LINEAR SOURCE UTEROVAGINAL APPLICATOR

Radiotherapy is and has been the treatment of choice in the management of invasive cancer of the uterine cervix for many years. A high percentage of cases can be cured when the disease is limited to the uterus and vagina. The risk of a tumor recurrence or therapeutic complication depends primarily on the ability of the radiotherapist to produce a dose distribution which eradicates the tumor and yet does not exceed normal tissue tolerances.

In some centers, linear source uterovaginal applicators are used in preference to nonlinear source applicators and have the following advantages:

A. Simpler and easier afterloading with radioactive sources;

B. Dose homogeneity around the entire circumference of the vaginal vault; and

C. Greater flexibility in fitting different anatomical sizes and disease distributions.

One of the basic principles of radiation treatment with a cylindrical applicator having a central linear source is to employ the greatest treatment distance (cylinder radius) which the patient's anatomy will permit. In this way, there is not such a precipitous fall in dose below the surface and the effective thickness of tissue which can be adequately irradiated is maximal.

Conventional linear source uterovaginal applicators are in the form of one-piece cylinders of varying lengths and diameters which slip over a tube (tandem) containing the central linear source and passing through the vagina into the uterine cavity. The diameter of the vaginal cylinder which may be used is limited by the size of the vaginal introitus, which in most instances is less than that of the vaginal vault.

My applicator uses two half-cylinders (bivoids) which are individually inserted through the vaginal introitus. Consequently, the diameter of vaginal cylinders which may be employed for treatment is limited only by the size of the vaginal vault—not the vaginal introitus.

Moreover, the rigid tandum of my applicator is fixed securely to a clamp overlying the perineum. The clamp is fastened with gauze straps to an elastic bandage around the patient's waist. In this manner, the intra-uterine portion of the tandem is held midway between the bladder anteriorly and the rectosigmoid posteriorly and overdosage of these structures is avoided.

The novel technical advances which distinguish my linear source uterovaginal applicator from the prior art are (a) improved percentage depth dose to the vagina by utilizing the maximum distance available between the radioactive source and vaginal mucosa, and (b) the capability of correcting retroversion or anteversion of the uterus during treatment.

In the drawing:

FIG. 1 is an exploded side-elevational view showing the components of my improved uterovaginal applicator, including the tandem itself with the bivoids removed, one bivoid, a bivoid holder, a linear source of radiant energy disassociated from the tandem, a completely assembled bivoid pair and a tandem clamp;

FIG. 2 is an elevational view showing the steps of mounting the bivoid pair on the tandem, although such assembly in the proper technique occurs within the vagina; and FIG. 3 is enlarged fragmentary elevational view of the tandem, partially in section, showing bivoids in place on the tandem; and FIG. 4 is a cross-sectional view taken along line 4—4 of FIG. 3.

A partially assembled uterovaginal applicator 10 as shown in FIG. 2 includes an elongated, tubular intravaginal tandem 12 that is adpated to receive a linear tube 14 (FIG. 1) containing multiple sources of radiant energy, such as cesium tubes 16, the tandem 12 terminating in a curved intrauterine portion 18. An enlargement, preferably in the form of a spherical ball 20 is attached rigidly to the tandem 12 adjacent the portion 18, and a pair of bivoids 24 and 26 surround the tandem 12 between the portion 18 and a transversely hexagonal sleeve 28 on the tandem 12 provided with a bevel 30 remote from the bivoid pair 24 and 26, such that the ball 12 is enclosed within the bivoid pair 24 and 26. A clamp 32 (FIG. 1) is also shown fragmentarily in FIG. 3 mounted on the sleeve 28. Screw threads 34 on that end of the tandem 12 opposite to the portion 18 are adapted to receive a closure cap 36 (FIGS. 1 and 2).

Each bivoid 24 and 26 has a semi-spherical, ball-receiving socket 38, a bore 40 that is transversely circular for receiving the tandem 12 and a cord loop 42 tied thereto adjacent its end 44 remote from socket 38. Each end 44 has the shape of one-half of a hemisphere.

Each of a pair of identical holders 46, one for each bivoid 24 and 26 respectively, includes an elongated rod 48 provided with a finger piece 50 on one of its ends, a crosshead 52 intermediate its ends (having a loop-receiving hook 54) and a cup-like head 56 on its opposite end provided with a cavity 58 for receiving a corresponding end 44. A loop clearance foramen 60 is provided in each of the heads 56.

The flexible, plate-like clamp 32 has concave edges and V-shaped ends as seen in FIG. 1 with an intermediate, longitudinally extending, sleeve-receiving slot 62, terminating in a widened portion within which is disposed a knurled turnknob 64 affixed to a screw 66 having left and right-hand threads meshed with nuts 68 mounted on the clamp 32. Corner holes 70 in the clamp 32 are adapted to receive gauze straps (not shown) which are, in turn, adapted to be fastened to an elastic bandage (not shown) around the patient's waist.

Technique of Application

Following the administration of a general anesthetic, the patient is placed in the dorsal lithotomy position. The perineum and vagina are washed with antiseptic solution. If urinary retention is expected, an indwelling catheter may be inserted; however, in most instances it will not be necessary. In order to obtain a clearer view of the cervix and vaginal fornices, a triple-bladed speculum is employed. The cervical canal is searched for with a uterine sound. Occasionally, when the canal is not readily apparent, one must hold the cervix with a single-tooth tenaculum, but this should be avoided if possible. Once the cervical canal has been identified, the uterine cavity is sounded and the depth noted. The canal is then progressively dilated, and the appropriate length tandem 12 is inserted into the uterine cavity.

The size of the vaginal bivoids 24, 26 which can be accommodated is estimated by the displacement of the three blades of the speculum and a little experience. Always the largest diameter possible should be selected, and the length should be such that the lowermost extent of the vaginal tumor does not extend beyond the center of the lowermost vaginal source. A large bivoid holder 46 is used for the 4.5 centimeter and 5.0 centimeter bivoids 24, 26 and a small holder 46 for the 3.0 centimeter, 3.5 centimeter, and 4.0 centimeter bivoids 24, 26. The pull strings 42 are passed through the foramens 60, looped over the hooks 54 and placed under tension. A bivoid 24 is inserted along the tandem 12 until the ball 20 in the upper vagina is seen to fall into the socket 38 of the bivoid 24. The bivoid 26 is then passed along the tandem 12 (FIG. 2) until it is felt to "pop" into place with the two bovoid holders 46 aligned on opposite sides of the tandem 12. Then the pull strings 42 are released and the bivoid holders 46 withdrawn, one at a time. A final look is taken to be sure the bivoids 24 and 26 are in proper position in relation to the tandem 12, encasing the ball 20.

When short bivoids 24, 26 are used, a short length of antiseptic-impregnated gauze is wrapped around the exposed tandem 12 and the pull strings 42 in the lower vagina. A suitable length of gauze is passed through each hole 70 of the clamp 32. The clamp 32 is placed loosely over the hexagonal sleeve 28 so that the bevel 30 is oriented upwardly. The bevel 30 indicates the direction of curvature of the intrauterine portion 18 of the tandem 12. The patient's legs are then lowered slowly to the supine position on the operating table. The tandem 12 and the loosened clamp 32 are allowed to come to a natural, comfortable position, then the clamp screw 66 is tightened securely. The four ends of the gauze straps are fastened to an elastic bandage around the patient's waist to hold the clamp 32 in place exteriorly of the vagina orifice across the external genitalia between the urethra and anal orifices. The patient may now lie on her back or either side in comfort, and she may empty her bladder or bowel in bed without soilage. En route from the recovery room to the ward room, radiographs are obtained to check the position of the tandem 12.

The applicator loadings and treatment times for each of two subcourses are obtained from the table corresponding to the particular combination of tandem and bivoids used. The first subcourse loading of the tandem 12 is inserted in the afternoon and is replaced with the second subcourse loading the following morning. The next day, the tandem 12 is removed at the patient's bedside. An anelgesic is not required. The gauze straps are cut; then the clamp 32 is loosened and removed. The protruding end of the vaginal gauze is pulled, bringing out the bivoid pull strings 42. One of the bivoid pull strings 42 is grasped and traction is exerted along the tandem 12. After "delivering" the first bivoid, the process is repeated for the second one. Finally, the tandem 12 is removed with a curvilinear motion so that the cervix is not traumatized.

While cesium-137 is indicated as a source of radiation because it is in common use, my invention comtemplates any radionuclide which spontaneously emits gamma rays including, but not limited to, cobalt-60 and radium-226. Readily available, however, are cesium-137 tubes constructed of two stainless steel capsules, including an inner core and an outer casing to insure the integrity of the source. Oftentimes, the source is loaded with thousands of cesium-labeled ceramic microspheres, resulting in a consistently uniform active length. Usually, each tube is engraved with a nominal activity and serial number, nickel-plated, and color-coded on the eyelet end of the source. The applicator 10 of my present invention, including the tandem 12 with its bivoids 24, 26 is especially adaptable for receiving various radiation therapy products such as cesium-137 brachytherapy sources.

The above-described method and apparatus for homogenously irradiating the vaginal mucosa with a linear source uterovaginal applicator maintains the vaginal vault distended by virtue of the bivoids on the tandem 12 itself such that, as above indicated, the maximum distance available between the source and the vaginal mucosa is utilized to provide an improved percentage depth dose to the vagina, as distinguished from linear source applicators heretofore suggested and employed in the treatment of malignant tumors of the human female genital organs.

I claim:

1. A therapeutic instrument for irradiative treatment of the genital tract by subjecting the same to radiant energy, said instrument comprising:
    an elongated, tubular, uterovaginal tandem terminating at the normally innermost end thereof in a tubular, intrauterine applicator,
    said tandem having an inlet at its normally outermost end adapting the tandem and its intrauterine applicator for afterloading with a linear source of radioactive energy having isodose curves in the form of concentric circles surrounding the same; and
    an enlarged, cylindrical, intravaginal applicator having an axial, tandem-receiving bore therethrough
    said intravaginal applicator completely surrounding and being coaxial with the tandem adjacent its intrauterine applicator,
    said intravaginal applicator having a pair of opposed, mating, initially separate, half-cylinder bivoids in abutting relationship along and longitudinally of the tandem, rendering said bivoids separately insertable into said vagina vault through said vaginal introitus and into place on the tandem after insertion of the tandam into said tract until its intrauterine applicator is disposed within the uterine cavity.

2. The invention of claim 1, said intravaginal applicator and said tandem having cooperating means for precluding displacement of the bivoids relative to the tandem when the intravaginal applicator is in surrounding relationship to the tandem.

3. The invention of claim 2, said cooperating means including a ball secured to and surrounding the tandem, said intravaginal applicator having a ball receiving socket and, except for said bore and socket, being otherwise solid, the entire external, cylindrical surface of the intravaginal applicator being smooth and uninterrupted.

4. The invention of claim 3, said ball being spherical and provided with a central, tandem-receiving passage conforming in internal diameter to the external diameter of the tandem; except for said passage, the ball being otherwise solid, said ball conforming in size and shape to that of the socket.

5. The invention of claim 1; and, in combination with said instrument, an inserter for each bivoid respectively, each inserter comprising an elongated rod for successively pushing its bivoid along the tandem in sliding relationship thereto until its bivoid is located adjacent the intrauterine applicator, each rod being provided with a head for receiving the proximal end of its bivoid.

6. The invention of claim 5, said ends of the bivoids having the shape of one-half of a hemi-sphere, each head having a cavity for receiving the corresponding bivoid end and conforming in shape therewith.

7. The invention of claim 5, each bivoid having means secured thereto and releasably attachable to the rod for holding the corresponding head against said proximal end during insertion.

8. The invention of claim 7, each releasable means being a cord loop, each rod having a loop-receiving hook remote from its head, each head being provided with a loop-clearing foramen.

9. The invention of claim 1; and an alongated, perineal member slidable along the tandem longitudinally thereof toward and away from the intravaginal applicator, said intravaginal applicator being disposed between its intrauterine applicator and said member, said member being provided with take-up means for clamping the same to the tandem in any one of a number of preselected positions therealong.

10. The invention of claim 9, said member having a longitudinal slot, said tandem being provided with a slot-receiving length having an irregular, transverse, external configuration for precluding rotation of the member around said length.

11. A method of irradiative treatment of the genital tract by subjecting the same to radiant energy, said method including the steps of:
   inserting an elongated, tubular, uterovaginal tandem into said tract through the vaginal introitus and thence through the cervical canal until a portion of the length of the tandem is disposed within the uterine cavity;
   inserting a sectional intravaginal applicator into said tract, having a pair of initially separate bivoids, until the applicator is in complete surrounding relationship to the tandem within the vaginal vault adjacent the cervix, by separately and successively sliding the bivoids along the tandem toward said portion of the length thereof; and
   loading the tandem with a linear source of radioactive energy having isodose curves in the form of concentric circles, whereby the maximum distance between said source and the vaginal mucosa is utilized to thereby provide for equal, regular and uniform, maximum percentage dose delivery of radiant energy to the entire circumference of the vagina.

12. The invention of claim 11, releasably connecting each bivoid to an inserter prior to bivoid insertion; actuating the inserters to push the bivoids along the tandem; releasing each bivoid from its inserter after the same is disposed within said vagina vault, and removing each inserter from said genital tract after each bivoid insertion.

13. The invention of claim 17; and sliding a retention member along the tandem into engagement with the perineum.

14. The invention of claim 13; and clamping the member to the tandem after it is in engagement with the perineum.

* * * * *